United States Patent [19]

Dooley et al.

[11] Patent Number: 5,006,554
[45] Date of Patent: Apr. 9, 1991

[54] ORGANOTIN COMPOUNDS

[75] Inventors: Carol A. Dooley; Elek Lindner, both of San Diego, Calif.

[73] Assignee: The United States of America as represented by the Secretary of the Navy, Washington, D.C.

[21] Appl. No.: 358,739

[22] Filed: May 26, 1989

[51] Int. Cl.$^5$ .......................... A01N 55.04; C07F 7/22; C09D 5/14

[52] U.S. Cl. .................................. 514/493; 514/494; 556/81; 556/94; 556/105; 106/15.05; 106/287.18

[58] Field of Search ...................... 514/493; 556/81, 94, 556/105

[56] References Cited

U.S. PATENT DOCUMENTS

| 2,702,778 | 2/1955 | Kerr et al. | 514/493 |
|---|---|---|---|
| 2,873,287 | 2/1959 | Ramsden | 260/429.7 |
| 3,222,158 | 12/1965 | Sowa | 514/493 |
| 3,388,179 | 6/1968 | Ramsden | 260/665 |
| 3,525,792 | 8/1970 | Leebrick | 514/493 |
| 3,794,501 | 2/1974 | De Nio | 106/15 |
| 4,010,141 | 3/1977 | Onozuka et al. | 260/45.75 |
| 4,021,392 | 3/1988 | Milne et al. | 260/28.5 |
| 4,475,941 | 10/1984 | Agglon et al. | 514/493 |

FOREIGN PATENT DOCUMENTS 0116615  6/1985  Japan ................................. 514/493

Primary Examiner—Stanley J. Friedman
Assistant Examiner—T. J. Criares
Attorney, Agent, or Firm—Harvey Fendelman; Thomas G. Keough

[57] ABSTRACT

Tributenyltin compounds containing double bonds at C-1 or C-3 or combinations thereof are synthesized from symmetrical tetrabutenyltins to offer a sufficient toxicity to function as a biocide or an antifoulant compound for ships' hulls and have an increased rate of degradation to be compatable with the environment.

1 Claim, No Drawings

5,006,554

ORGANOTIN COMPOUNDS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The use of tributyltin compounds as antifoulants for ships' hulls has become of increasing concern because of their potential toxicity to non-target organisms and because of the potential for bioaccumulation. It is known that when ethyl and propyl groups are replaced by vinyl and allyl groups in tetraorganotins, the resulting double-bonded compounds show enhanced chemical reactivity. In an attempt to create more reactive compounds, this invention synthesizes organotin compounds in which butyl groups are replaced with butenyl groups. Such compounds, used as antifoulants, show promise as being able to degrade more quickly in the environment while retaining sufficient toxicity to target organisms.

SUMMARY OF THE INVENTION

The present invention is directed to providing a biocide or antifoulant for a ship's hull to reduce the effects of marine fouling in the ocean and which includes trialkyl compounds containing double bonds at carbon atoms C-1 or C-3 or a combination thereof.

An object of the invention is to provide an antifoulant coating for ships' hulls that is less harmful to the environment by virtue of being more rapidly degradable.

Another object of the invention is to provide an antifoulant compound having a faster degradation rate with acceptable toxicity than contemporary antifouling compounds.

Yet another object is to provide a new class of organotin compounds in which the organic moieties are unsaturated to provide appropriate levels of antifouling protection with lower levels of environmental contamination.

Yet another object of the invention is to provide an antifoulant coating including tributenyltin compounds.

These and other features, objects, and advantages of the present invention will be better appreciated from an understanding of the operative principles of a preferred embodiment as described hereinafter.

DESCRIPTION OF THE PREFERRED EMBODIMENT

Since the triorganotin compounds are synthesized from symmetrical tetraorganotins, the procedure for the preparation of the tetrabutenyltins necessarily must be performed first to produce tributenyltins.

Tetraorganotins commonly are prepared by reaction of the appropriate Grignard reagent with anhydrous tin(IV) chloride ($SnCl_4$) or with organotin halides to obtain symmetrical and unsymmetrical tetraorganotins. Compounds, such as tetraallyltin, tetravinyltin, but-3-enyltriphenyltin and many more have been prepared by this method. Two routes to the synthesis of triorganotin halides have been generally used on a laboratory scale: the redistribution reaction between tetraorganotin ($R_4Sn$) and tin(IV) chloride ($SnCl_4$) or selective cleavage of the tetraorganotin with hydrogen halide or halogen.

1-Bromo-1-butene, 4-bromo-1-butene and 1-chloro-2-butene were obtained from a commercial supplier, Pfaltz and Bauer (Waterbury, Conn., USA). Resublimed magnesium chips, tetrabutyltin [$(CH_3CH_2CH_2CH_2)_4Sn$], and tributyltin bromide [$(CH_3CH_2CH_2CH_2)_3SnBr$], also were obtained from a commercial supplier, Alfa Products (Danvers, Mass., USA). All were used, as to be elaborated on below, without further purification.

For synthesis of tetra-1-butenyltin [$(CH_3CH_2CH=CH)_4Sn$] and tetra-3-butenyltin ($CH_2=CHCH_2CH_2)_4Sn$], a Grignard reagent was prepared by the dropwise addition of approximately 10 g of 1-bromo-1-butene or 4-bromo-1-butene in 10 cm$^3$ anhydrous tetrahydrofuran to an excess of magnesium chips, which were just covered with tetrahydrofuran and kept under dry argon. After adding the alkenyl halide, the mixture was maintained at reflux for 4 h. For preparation of tetra-2-butenyltin, ($Ch_3CH=CHCH_2)_4Sn$, the Grignard reagent was formed from 1-chloro-2-butene. After initiation of the reaction, the reagent was immediately cooled to $-10°$ C. and stirred at that temperature for 9 h during and after the addition of 1-chloro-2-butene.

To prepare the tetra-alkenyltin compound, the Grignard reagent was first decanted from the excess magnesium chips, then cooled to 0° C. Approximately 2 g of anhydrous $SnCl_4$ in 10 cm$^3$ of hexane was added dropwise to the stirred solution. The mixture was refluxed for 4 h and then left at room temperature overnight.

The reaction mixture was cooled to 0° C. and hydrolyzed with 3% hydrochloric acid (HCl). The separated organic layer was shaken with 5% aqueous potassium fluoride (KF) to precipitate organotin chlorides or bromides as insoluble fluorides. The solvent and low-boiling side-products were then removed under vacuum at room temperature from the separated organic layer, and the residue was washed through a 22 cm × 1 cm Florisil column with hexane. The solvent was again removed under vacuum.

The tri-n-alkenyltin bromides are synthesized by taking approximately 1 g of the tetra-alkenyltin and suspending it in 10 cm$^3$ methanol. A stoichiometric amount of bromine in methanol was added dropwise in dim light to the stirred tetrabutenyltin mixture. Monobromination of the tetraalkenyltin to form tri-1-butenyltin bromide [$(CH_3CH_2CH=CH)_3SnBr$], tri-2-butenyltin bromide, [$(CH_3CH=CHCH_2)_3SnBr$] and tri-3-butenyltin [$(CH_2=CHCH_2CH_2)_3SnBr$] bromide was achieved by conducting the reaction at 0, $-50$ and 20° C., respectively. Upon completion of the reaction, the solvent and low-boiling side-products were removed under vacuum at room temperature. The crude product was washed through a Florisil column first with hexane to recover unreacted tetraalkenyltin and then with 1:4 (v/v) ethyl acetate/hexane to elute selectively the trialkenyltin bromide. Solvent was then removed under vacuum.

Degradation tests of the compounds included making ethanol solutions of the organotin bromides that were prepared at a concentration of approximately 1 mg/cm$^3$. Aliquots of the ethanol solutions were added to either 3.5% sodium bromide (NaBr) containing 1% acetone or to filtered seawater to obtain approximately 1–5 ppm concentrations in the seawater. The sodium bromide (NaBr) solution was placed in 125 cm$^3$ quartz tubes and exposed to sunlight over 48 h. The seawater solutions were kept in closed 500 cm$^3$ polycarbonate jars in the laboratory. Aliquots (10 cm$^3$) of the solutions were extracted at timed intervals with 1 cm$^3$ hexane after acidification with 0.1 cm$^3$ concentrated hydrochloric acid (HCl). Samples were analyzed by GC MS.

Relative toxicity of compounds was determined using a Microtox Toxicity Analyzer Model 2055, manufactured by Microbics Corporation, Carlsbad, Calif., USA. This bioassay measures the relative reduction in light output by a luminescent bacterium, Photobacterium phosphoreum NRRL B-11177, when exposed to a toxicant. The bacteria are provided in a convenient freeze-dried form by Microbics Corporation and are immediately activated by the addition of 1 cm$^3$ of distilled water.

For Microtox testing, stock solutions of the compounds were prepared in 95% ethanol at approximately 1-2 mg/cm$^3$ Appropriate amounts of the ethanol solutions were added to 2% aqueous sodium chloride (NaCl) to achieve a workable concentration while keeping the ethanol concentration as low as possible. Typically, the ethanol concentration was about 0.05%.

Serial dilutions of each compound for measurement were performed in the Microtox photometer/incubator at 15° C. Controls consist of triplicate 1 cm$^3$ portions of 2% sodium chloride and candidate toxics were prepared in and subsequently serially diluted in 2% sodium chloride, with a final volume of 1 cm$^3$ for each dilution. After a 5-minute period for temperature equilibration, 10 μl of rehydrated bacteria was added to each of the controls and the serial dilutions of the test compound. Measurements in the photometer were made at 5 and 15 minutes after addition of the reagent. This procedure was repeated at least four separate times for each compound to provide four independent toxicity values.

The toxicity value is expressed as an EC$_{50}$ concentration, which is the concentration of a compound which caused a 50% reduction in light output. The EC$_{50}$ concentrations were determined by graphic interpolation on log-log paper, plotting the gamma-function against concentration. The gamma-function is the ratio of the amount of light lost to the amount of light remaining. A gamma-value of 1 corresponds to a 50% reduction in light, or EC$_{50}$.

The retention times and mass spectra of synthesized and purchased compounds were obtained with a Hewlett-Packard Model 5890A Gas Chromatograph directly connected to a Hewlett-Packard Model 5970 Mass Selective Detector (GC-MS). Data collection and reduction were performed with a Hewlett-Packard 9000-300 Computer using Model 59970C ChemStation software. Samples were run using splitless injection onto a 12.5 m × 0.2 mm (i.d.) HP1 fused silica capillary column with 0.33 μm coating thickness. Helium carrier gas was used at a head pressure of 40 kPa. The oven was programmed, after an initial 2-minute hold at 50° C. at 30° C./min. Injector, transfer line and detector were at 250° C. Masses were scanned between 50 and 450 amu. Electron energy is fixed at 70 eV for this instrument.

Infrared (IR) spectra were obtained using a Digilab FTS-60 Fourier Transform IR Spectrometer interfaced with a HewlettPackard Model 5890A Gas Chromatograph at the chromatographic conditions detailed above. Spectra are obtained in a 250° C. cell composed of gold-coated capillary-glass tubing.

Synthesis of the tetrabutenyltins presented no great difficulty as long as the Grignard reagent was present in large excess to assure complete alkylation. The tetrabutenyltins were all stable as neat compounds and in inert solvents. The tributenyltin bromides exhibited considerable variation in stability. Tri-2-butenyltin bromide was so reactive with the synthesis side-products that it could not be isolated, although gas chromatographic retention times and mass spectra could be obtained on products in the reaction mixture. Tri-1-butenyltin bromide, and to a lesser extent, Tri-3-butenyltin bromide tended spontaneously to form black precipitates during solvent evaporation of the crude mixture prior to column chromatography clean-up, if the distillation flask were warmed. Under these conditions alkenyltin compounds were identified containing various numbers of eight carbon groups in the mixture. Once purified, tri-3-butenyltin bromide and tri-1-butenyltin bromide were stable as neat compounds and in inert solvents.

Progress of the synthesis reactions and purity of the products were monitored using GC MS. Differentiation of the tetrabutenyltins and tributenyltin bromides was achieved by gas chromatographic retention times, mass spectrometry and IR spectrometry. Where cis-trans isomers were present in the starting butenyl halides, a mixture of isometric butenyltins was formed. Although these isomers could be separated by gas chromatography, there was no attempt to separate them chemically and purify them. These isomers are responsible for the multiple retention times listed in Table 1. Mass spectra of stereoisomers were identical.

TABLE 1

| Compound | GC retention times<br>Retention times (min) |
|---|---|
| Tetrabutyltin | 7.23 |
| Tetra-1-butenyltin | 7.06, 7.10 |
| Tetra-2-butenyltin | 8.27, 8.45, 8.65, 8.87, 9.07 |
| Tetra-3-butenyltin | 7.34 |
| Tributyltin bromide | 7.30 |
| Tri-1-butenyltin bromide | 7.09 |
| Tri-2-butenyltin bromide | 8.12, 8.25, 8.40, 8.56 |
| Tri-3-butenyltin bromide | 7.24 |

Tetra-alkyltins exhibit mass spectra (MS) characterized by the successive loss of alkyl groups from the tin atom. Typically, the parent ion is weak or non-existent; there is low abundance of ions from fragmentation of the alkyl chain; and the favored ions are tri- and mono-coordinated tin. Trialkyltin halides show a similar MS fragmentation pattern where successive loss of the alkyl groups is favored over loss of the halide ion. Qualitatively, the mass spectra of the tetrabutenyltins and tributenyltin bromides resemble those of the fully saturated analogues in their fragmentation patterns. In general, these spectra are characterized by analogous clusters of tin-containing fragments with two less mass units (H atoms) per attached carbon chain than the tetrabutyltin.

The relative intensities of the major fragment ions, normalized to the largest peak occurring between m/z 100 and 350 for tetrabutyltin and the tetrabutenyltins are shown in Table 2. The unique ion ratios for each compound show that the precursor tetra-alkenyltin compounds are different from each other and different from the fully saturated tetrabutyltin.

TABLE 2

| | Fragment ion intensities of $R_4Sn$ | | | | | | | |
|---|---|---|---|---|---|---|---|---|
| | $SnH_i^+$ | | $RSnH_i^+$ | | $R_2SnH_i^+$ | | $R_3Sn^+$ | |
| R group | m/z | Rel. int. | m/z | Rel. int. | m/z | Rel. int. | m/z | Rel. int. |
| Butyl | 121 | 67 | 179 | 100 | 235 | 66 | 291 | 49 |
| 1-Butenyl | 120 | 59 | 175 | 44 | 231 | 41 | 285 | 100 |
| 2-Butenyl | 121 | 22 | 175 | 100 | 230 | 7 | 285 | 35 |
| 3-Butenyl | 121 | 38 | 175 | 81 | 231 | 20 | 285 | 100 |

$i = 0-3$.

The fragmentation patterns of tributyltin bromide and tributenyltin bromides are dominated by tin-bromine (SnBr)containing ions and resemble each other to the same extent as the tetra-alkyltin compounds. Major ion fragments are summarized in Table 3 for tributyltin bromide, tri-1-butenyltin bromide, tri-2-butenyltin bromide and tri-3-butenyltin bromide.

TABLE 3

| | Fragment ion intensities for $R_3SnBr$ | | | | | | | | | |
|---|---|---|---|---|---|---|---|---|---|---|
| | $SnH_i^+$ | | $RSnH_i^+$ | | $SnBr^+$ | | $RSnBrH_i^+$ | | $R_2SnBrH_i^+$ | |
| R group | m/z | Rel. int. | m/z | Rel. int. | m/z | Rel. int. | m/z | Rel. int. | m/z | Rel. int. |
| Butyl | 121 | 21 | 177 | 21 | 199 | 49 | 257 | 45 | 313 | 100 |
| 1-Butenyl | 121 | 29 | 175 | 39 | 199 | 98 | 255 | 11 | 309 | 100 |
| 2-Butenyl | 121 | 12 | 175 | 36 | 199 | 100 | 254 | 10 | 309 | 28 |
| 3-Butenyl | 121 | 19 | 175 | 63 | 199 | 52 | 255 | 4 | 309 | 100 |

$i = 0-3$.

Since double-bond migration is a common occurrence under electron impact, the double-bond position in the parent compound cannot be directly determined by the presence or absence of distinctive ion fragments. Infrared spectrometry was used to determine the position of the double bond and to show that this position was retained after bromination of the compound. These data are summarized in Table 4 as the vibration of the carbon-carbon double bond (C=C) in alkenyltin compounds. These IR vibrations compare favorably with those reported for similar compounds in the literature.

TABLE 4

| IR bands of alkenyltin compounds | |
|---|---|
| Compound | $v(C=C)$ (cm$^{-1}$) |
| $(CH_3CH_2CH=CH)_4Sn$ | 1597.1 |
| $(CH_3CH_2CH=CH)_3SnBr$ | 1600 |
| $(CH_3CH=CHCH_2)_4Sn$ | 1647 |
| $(CH_2=CHCH_2CH_2)_4Sn$ | 1639.5 |
| $(CH_2=CHCH_2CH_2)_3SnBr$ | 1639.5 |

The tributenyltins exhibit considerable variation in stability and chemical reactivity. As mentioned above, tri-2butenyltin bromide, an allylic compound, was highly reactive and therefore transient; the compound readily underwent redistribution reactions with side-products of the synthesis reactions, and so could not be isolated. The other two tributenyltin bromides were stable as neat compounds, in inert solvents and in ethanol for a reasonable length of time. Chemical reactivity appeared to follow the order allyl > vinyl > alkyl. The tri-3-butenyltin bromide fell between tri-1-butenyltin bromide, containing vinylic carbons, and tributyltin bromide, the alkyl compound.

Upon exposure to direct sunlight, seawater solutions of tri-1-butenyltin bromide and tri-3-butenyltin bromide in quartz tubes showed about 80% and 100% loss of compound, respectively, after 48 h; tributyltin bromide showed a loss of only about 15% over the same period. Half-lives of 33 days, 17 days and 16 days were estimated for tributyltin bromide, tri-3-butenyltin bromide and tri-1-butenyltin bromide in seawater, protected from UV light and held at a constant room temperature.

Relative toxicities of the new compounds were determined by using the Microtox Toxicity Analyzer. As mentioned above, the toxicity value is expressed as an $EC_{50}$, the concentration of the compound which causes a 50% reduction in light output. The results are shown in Table 5 as $EC_{50}$ values at 5 min and 15 min.

TABLE 5

| Toxicity of tributyl- and tributenyl-tin bromides | | |
|---|---|---|
| Compound | 5-min $EC_{50}$ ($\mu$mol dm$^{-3}$) | 15-min $EC_{50}$ ($\mu$mol dm$^{-3}$) |
| $(CH_3CH_2CH_2CH_2)_3SnBr$ | 0.13 ± 0.01 | 0.06 ± 0.02 |
| $(CH_3CH_2CH=CH)_3SnBr$ | 0.82 ± 0.16 | 0.44 ± 0.04 |
| $(CH_2=CHCH_2CH_2)_3SnBr$ | 0.44 ± 0.05 | 0.27 ± 0.03 |

A low $EC_{50}$ indicating a more toxic compound, tri-1-butenyltin bromide and tri-3-butenyltin bromide were less toxic than tributyltin bromide by factors of about three and six, respectively.

Tributenyltin bromides containing double bonds at C-1 and C-3, synthesized from symmetrical tetrabutenyltins, were sufficiently stable for degradation and toxicity determinations. Tri-2-butenyltin bromide was too reactive for other than structural studies. Both tri-1-butenyltin bromide and tri-3-butenyltin bromide were less stable in seawater, in the presence and absence of light, than tributyltin bromide. The relative toxicities of the tributenyltin bromides, determined using a bioluminescent bacteria assay, were somewhat lower than that of tributyltin bromide.

A biocide or antifoulant for a ship's hull to reduce the effects of marine organisms in the ocean includes tributenyltin bromides having double bonds at carbon atoms C-1 or C-3. The tributenyltin bromides having double bonds at carbon atoms C-1 or C-3 allow their use in environmentally acceptable applications. On the basis of the above properties, the new compounds appear to satisfy the requirements for a good antifoulant. The desirable requirements are rapid degradation in the environment to a non-toxic form after acting on target organisms.

The invention may be practiced other than specifically disclosed and be within the scope of the claims.

I claim:

1. A method of reducing marine organisms on a ship's hull which comprises administering an effective amount of tributenyltin bromides having double bonds at carbon atoms C-1 or C-3 to remove said organisms from a ship's hull.

* * * * *